United States Patent [19]

Hübl et al.

[11] Patent Number: 5,064,847
[45] Date of Patent: Nov. 12, 1991

[54] 5-SUBSTITUTED 3-ARYLISOXAZOLE DERIVATIVES, THEIR PREPARATION AND THEIR USE AS PESTICIDES

[75] Inventors: Dieter Hübl, Werne; Ernst Pieroh, Risum-Lindholm, both of Fed. Rep. of Germany

[73] Assignee: Schering Aktiengesellschaft, Fed. Rep. of Germany

[21] Appl. No.: 517,362

[22] Filed: May 1, 1990

[30] Foreign Application Priority Data

May 2, 1989 [DE] Fed. Rep. of Germany ....... 3914969

[51] Int. Cl.$^5$ ..................... A61K 31/44; A61K 31/42; C07D 261/12; C07D 413/04
[52] U.S. Cl. .................................. 514/380; 514/340; 546/275; 548/243
[58] Field of Search ................ 548/243; 514/380, 340; 546/275

[56] References Cited

U.S. PATENT DOCUMENTS

| | | | |
|---|---|---|---|
| 3,781,438 | 12/1973 | Gibbons | 514/378 |
| 3,879,532 | 4/1975 | Hass et al. | 514/378 |
| 3,879,533 | 4/1975 | Carr et al. | 514/378 |
| 4,000,150 | 12/1976 | Cambon et al. | 548/243 |

Primary Examiner—Mukund J. Shah
Assistant Examiner—E. Bernhardt
Attorney, Agent, or Firm—Ostrolenk, Faber, Gerb & Soffen

[57] ABSTRACT

There are described new 5-substituted 3-arylisoxazole derivatives of general formula I

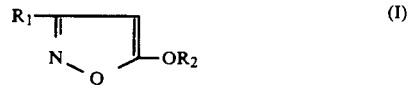

in which in which $R_1$ and $R_2$ have the meanings given in the description, processes for their preparation and their use as pesticides, especially against nematodes.

12 Claims, No Drawings

5-SUBSTITUTED 3-ARYLISOXAZOLE DERIVATIVES, THEIR PREPARATION AND THEIR USE AS PESTICIDES

The invention relates to new 5-substituted 3-arylisoxazole derivatives, their preparation as well as their use as pesticides, especially against nematodes.

Arylisoxazoles with nematicidal activity are already known, eg as in U.S. Pat. No. 3,781,438.

The disadvantage of the known componds however is that they are not sufficiently tolerant to plants or are sufficiently active.

The object of the present invention is to provide compounds that have especially good accivity against nematodes at the same time being intolerant to plants.

It has now been found that 5-substituted 3-arylisoxazole derivatives of general formula I

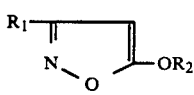

wherein $R_1$ is phenyl, biphenyl, naphthyl, furyl, thienyl or pyridyl, each of which is optionally substituted by one or more, of the same or different, halogen, $C_{1-14}$-alkyl, $C_{3-6}$-cycloalkyl, $C_{1-4}$-alkoxy, $C_{1-4}$-alkylthio, di-$C_{1-4}$-alkylamino, $C_{1-6}$-alkoxycarbonyl, halo-$C_{1-4}$-alkyl, halo-$C_{1-4}$-alkoxy, halo-$C_{1-4}$-alkylthio, halo-$C_{1-6}$-alkoxycarbonyl, halo-$C_{3-6}$-cycloalkyl, halo-$C_{3-6}$-cycloalkylmethoxy, halo-$C_{3-6}$-cycloalkylmethylthio, nitro, cyano, amino, phenoxy, halophenoxy, phenylthio or halophenylthio groups, and $R_2$ is $C_{1-12}$-alkyl, $C_{2-12}$-alkenyl, $C_{2-12}$-alkynyl, $C_{3-6}$-cycloalkyl or $C_{3-6}$-cycloalkylmethyl, each of which is substituted one or more times by the same or different halogen, show a surprisingly good nematicidal activity coupled with good plant compatibility.

The compounds of the invention also good activity against biting and sucking insects and their eggs and also mites.

The term "haloalkyl" means that one or more hydrogen atoms of the alkyl group are replaced by halogen. By halogen is meant Cl, F, Br or I.

The compounds of the invention of general formula I can be prepared according to known methods by reacting compounds general formula II,

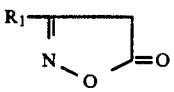

in which $R_1$ has the meaning given in formula I, with compounds of formula Z-$R_2$, in which Z is a leaving group such as for example halogen, mesylate and tosylate and $R_2$ has the meaning given above, in an inert solvent or solvent mixture, preferably at raised temperature and preferably at raised pressure, in the presence of a base.

Suitable bases include organic and inorganic bases, such as for example tertiary amines, eg triethylamine or tripropylamine, alkali metal and alkaline earth metal hydrides, hydroxides, carbonates and bicarbonates and also alkali metal alcoholates, such as sodium methoxide or potassium tert.-butylate.

Suitable solvents for the preparation of the compounds of the invention include for example diethyl ether, dioxane and tetrahydrofuran; aliphatic and aromatic hydrocarbons, such as toluene and petroleum ether; halogenated hydrocarbons, eg chlorobenzene, methylene chloride, carbon tetrachloride and chloroform, nitriles such as acetonitrile and propionitrile; N,N-dialkylamides, such as for example dimethylformamide; ketones, such as acetone and methyl ethyl ketone; dimethyl sulphoxide, sulpholane, as well as water and alcohols, eg methanol, ethanol, isopropanol or butanol, and mixtures of such solvents.

The reaction temperature depends on the reactants and can vary between −70° C. and 120° C. The pressure also depends on the reactants and can lie between 1 and 25 bar. The reaction usually lasts from ca. 0.5 to 48 hours. The reaction mixture can be poured into ice/water, extracted and worked up in known manner. The resulting products can be purified in conventional manner, for example by recrystallisation, vacuum distillation or column chromatography.

The compounds of formula II used as starting material are either known or can be obtained in an analogous way to known processes (eg U.S. Pat. No. 3,781,438; Chem. Ber. 110, 2922–2938 (1977) and J. Chem. Soc. 1971, 1945).

Because of the nematicidal activity coupled with good plant compatibility, the compound according to the invention can be successfully applied in plant protection as pesticides in agriculture, in vine and fruit growing, in horticulture and in forestry.

Plant parasitic nematodes which can be controlled according to the invention include for example root-knot nematodes, such as *Meloidogyne incognita, Meloidogyne hapla* and *Meloidogyne javanica,* cyst forming nematodes, such as *Globodera rostochiensis, Heterodera schacktii, Heterodera avanae, Heterodera glycines* and *Heterodera trifolii,* and stem and leaf eelworms, such as *Ditylenchus dipsaci, Ditylenchus destructor, Aphelenchoides ritzemabosi, Pratylenchus neglectus, Pratylenchus penetrans, Pratylenchus curvitatus,* as well as *Tylenchorhynchus dubius, Tylenchorhynchus claytoni, Rotylenchus robustus, Heliocotylenchus multicinctus, Radopholus similis, Belonolaimus longicaudatus, Longidorus elongatus* and *Trichodorus primitivus.*

Based on their insecticidal and acaricidal properties, the compounds of the invention further offer the possibility of treatments against pests in the different stages of crops as well as human and animal pests.

The use of the active ingredients of the invention can be carried out in the form of their conventional commercial formulations and/or the ready to use preparations from these formulations.

The content of active ingredient in the ready to use preparations obtained from the commercial concentrated formulations can vary over wide ranges. The rate of use for the control of nematodes lies between 0.03 kg to around 10 kg per hectare, preferably from around 0.3 kg to around 6 kg per hectare.

The active ingredient or their mixtures can be applied in the usual formulations such as solutions, emulsions, wettable powders, suspensions, powders, dusts, foams, pastes, soluble powders, granules, aerosols, suspension concentrates, seed dressings, natural and synthetic substances impregnated with the active ingredients, microcapsules in polymers and in seed coatings for seeds, as well as formulations with burning substances such as smoke cartridges, smoke capsules and smoke spirals amongst others as well as ULV-cold and hot fogging formulations.

These formulations can be prepared in known manner for example by mixing the active ingredient with diluents such as liquid solvents, and liquefied gases and/or solid carriers, optionally using surface active agents such as emulsifiers and/or dispersing agents and/or foaming agents.

When using water as the diluent, organic solvents can also be used for example as auxiliary solvents.

Examples of liquid solvents include aromatic hydrocarbons, such as xylene, toluene or alkynaphthalenes, chlorinated aromatic or chlorinated aliphatic hydrocarbons, such as chlorobenzene, chloroethylene or methylene dichloride, aliphatic hydrocarbons, such as cyclohexane or paraffins, for example mineral oil fractions, alcohols, such as butanol and glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

By the term liquefied gaseous diluents or carriers are meant those substances which are gaseous at normal temperature and pressure, for example aerosol blowing agents, such as halohydrocarbons, as well as butane, propane, nitrogen and carbon dioxide.

Examples of solid carriers are natural earth powders, such as kaolin, alumina, talc, chalk, quartz, attapulgite, montmorillonite or diatomaceous earths and synthetic powders, such as finely divided silica, aluminium oxide and silicates as well as solid carriers for granules, crushed and fractionated natural rocks, such as calcite, marble, pumice, sepiolith and dolomite, as well as synthetic granules from inorganic and organic powders as well as granules from organic materials such as sawdust, coconut shells, maize cobs and tobacco stalks.

Examples of emulsifying and/or foaming agents include non-ionic and anionic emulsifiers, such as polyoxyethylene-fatty acid esters, polyoxyethylene-fatty alcohol ethers, for example alkylaryl-polyglycol-ethers, alkylsulphonates and arylsulphonates as well as protein hydrolysates.

Dispersing agents include for example lignin, sulphite waste liquors and methylcellulose.

There can also be used in the formulations sticking agents such as carboxymethylcellulose, natural and synthetic powdery, granulated or latex-forming polymers, as well as gum arabic, polyvinyl alcohol and polyvinyl acetate.

There can also be used dyestuffs, such as inorganic pigments, for example iron oxide, titanium oxide, ferrocyan blue and organic dyestuffs such as alizarin- and azo-metal phthalocyanine dyestuffs and trace elements such as salts of iron, manganese, boron, copper, cobalt, molybdenum and zinc.

The formulations contain in general between 0.1 and 95 weight percent of the active ingredient, preferably between 0.5 and 90 percent.

Examples of formulations are:
I. Wettable powder 10 parts by weight of the compound of Example 1 were intimately mixed with 12 parts by weight of calcium lignosulphonate, 76 parts by weight of finely divided kaolin and 2 parts by weight of dialkylnaphthalene sulphonate and then milled.

II. Dusting powder 2.5 parts by weight of the compound of Example 1 were dissolved in 10 methylene chloride and added to a mixture of 25 parts by weight of finely divided silicic acid and 71.5 parts by weight talc and 1 part by weight sudan red. The solvent was removed in vacuo and the residue finely milled.

III. Granule 5 parts by weight of the weight of the compound of Example 1 were dissolved in 10 parts by weight of methylene chloride and sprayed onto 95 parts by weight granulated attapulgite of particle size 0.3–0.8 mm and dried.

IV. Emulsifiable concentrate 20 parts by weight of the compound of Example 1 were dissolved in a mixture of 75 parts by weight of isophorone and 5 parts by weight of a mixture of 30 parts by weight of calcium benzene sulphonate and 30 parts by weight of castor oil polyglycolate with 40 mole % ethylene oxide and 40 parts by weight of a copolymer of propylene- and ethylene oxide.

The following Examples illustrate the preparation of compounds of the invention.

PREPARATION EXAMPLE 1

3-(4-Chlorophenyl)-5-difluoromethoxyisoxazole

In a 100 ml autoclave, 5.87 g (0.03 mol) 3-(4-chlorophenyl)-5-(4H)-isoxazolone was dissolved 30 ml dioxane and treated with 10 ml of 30% aqueous potassium hydroxide. The autoclave was pressurised to 10 bar with chlorodifluoromethane and the reaction mixture was heated at 50°–60° C. for 15 hours. After cooling and reducing the pressure the solution was poured into 300 ml ice/water and extracted three times with 70 ml ethyl acetate. The combined organic phases were dried over magnesium sulphate and concentrated. The residue was purified by column chromatography.

Yield: 1.20 g = 16.3% of theory
mp: 52° C.

PREPARATION EXAMPLE 2

5-Bromodifluoromethoxy-3-(4-chlorophenyl)isoxazole 1.5 g (0.05 mol) of an 80% suspension of sodium hydride in paraffin oil, which had been washed with 10 ml toluene, was suspended in 50 ml dimethylformamide. At a temperature of 10°–20° C., a solution of 5.0 g (0.026 mol) 3-(4-chlorophenyl)-5(4H)-isoxazolone in 40 ml dimethylformamide was added dropwise and the mixture stirred for 1 hour. 10.75 g (0.052 mol) dibromodifluoromethane was added dropwise and the mixture stirred for 2 hours at room temperature. The mixture was added to 300 ml ice/water and extracted three times with 100 ml ethyl acetate. The combined organic phases were dried over magnesium sulphate and concentrated. The residue was purified by column chromatography (eluent: hexane/diethyl ether 9:1).

Yield: 1.2 g = 14% of theory
$n^{20}_D$ 1.54550

In a similar manner, the following compounds were prepared.

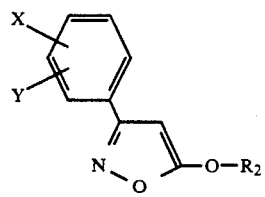

| Example No. | X | Y | $R_2$ | mp (°C.)/$n_D^{20}$ | |
| --- | --- | --- | --- | --- | --- |
| 3 | 4-Cl | H | $CF_2=CF(CH_2)_2$ | 63 | |
| 4 | 4-Cl | H | F-cyclopropyl(F)-CH$_2$ | 85 | |
| 5 | 4-Cl | H | $CF_3-(CH_2)_3$ | 80 | |
| 6 | 4-Cl | H | $FCH_2CH_2$ | 91 | |
| 7 | H | H | $CHF_2$ | 43–45 | |
| 8 | H | H | $CF_2=CF-(CH_2)_2$ | 83 | |
| 9 | H | H | $CF_2Br$ | | 1,5161 |
| 10 | H | H | F-cyclopropyl(F)-CH$_2$ | 90–02 | |
| 11 | 3-Cl | H | $CF_2Br$ | | 1,5387 |
| 12 | 3-Cl | H | $CF_2=CF-(CH_2)_2$ | 52–54 | |
| 13 | 2-Cl | H | $CF_2=CF(CH_2)_2$ | | 1,5216 |
| 14 | 3-Cl | H | $CF_2$ | | 1,5187 |
| 15 | 2-Cl | H | $CF_2$ | | 1,5183 |
| 16 | 2-Cl | H | $CF_2Br$ | | 1,5286 |
| 17 | 4-OCH$_3$ | H | $CF_2=CF(CH_2)_2$ | 66–69 | |
| 18 | 4-OCH$_3$ | H | $CF_2Br$ | | 1,5413 |
| 19 | H | H | $CH_2=CCl-CH_2$ | 58–60 | |
| 20 | H | H | $ClCH=CH-CH_2$ | 28–30 | |
| 21 | 4-Cl | 2-Cl | $CF_2=CF(CH_2)_2$ | | 1,5374 |
| 22 | 4-Cl | 2-Cl | $CF_2Br$ | | 1,5339 |
| 23 | 4-F | H | $CF_2Br$ | | 1,4797 |
| 24 | 4-F | H | $CF_2=CF(CH_2)_2$ | 58–59 | |
| 25 | 4-Cl | 2-Cl | $CF_2$ | | 1,5418 |
| 26 | 4-F | H | $CF_2$ | | 1,5016 |
| 27 | 4-CH$_3$ | H | $CF_2=CF(CH_2)_2$ | 84–86 | |
| 28 | 4-CH$_3$ | H | $CF_2$ | 49–51 | |
| 29 | 4-CH$_3$ | H | $CF_2Br$ | | 1,5293 |
| 30 | 3-F | H | $-CH_2CH_2-CHF=CF_2$ | 63–65 | |
| 31 | 3-F | H | $-CF_2Br$ | | 1,5136 |
| 32 | 3-F | H | $-CHF_2$ | | 1,5023 |
| 33 | 4-CF$_3$ | H | $-CHF_2$ | 40–41 | |
| 34 | 4-CF$_3$ | H | $-CH_2-CH_2-CHF=CF_2$ | 60–62 | |
| 35 | 3-Cl | 4-Cl | $-CH_2-CH_2-CHF=CF_2$ | 39–41 | |
| 36 | 3-Cl | 4-Cl | $-CHF_2$ | 47–48 | |
| 37 | 2-F | 6-F | $-CH_2-CH_2-CHF=CF_2$ | 61–63 | |
| 38 | 2-F | 6-F | $-CHF_2$ | 42–45 | |
| 39 | 4-CF$_3$ | H | $-CF_2Br$ | | 1,48518 |
| 40 | 3-Cl | 4-Cl | $-CF_2Br$ | | 1,56158 |
| 41 | 2-F | H | $-CHF_2$ | | 1,50352 |
| 42 | 2-F | H | $-CF_2Br$ | | 1,51036 |
| 43 | 2-F | H | $-CH_2-CH_2-CHF=CF_2$ | 66–68 | |

The following use examples illustrate the biological activity of the compounds of the invention.

USE EXAMPLE A

Control of root knot nematode, *Meloidogyne incognita*

5% of a powder preparation of the active ingredient was mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25 to 28 days the cucumber roots were washed and inspected in a water bath for nematode attack (root knots) and the % level of activity of the active ingredients compared with a treated control was determined. When the nematode attack is fully controlled the level of activity is 100%.

At a dose of 25 mg or less of active substance per liter of soil, a nematode attack by *Meloidogyne incognita* was fully controlled (90–100%) the compounds of Examples 2, 3, 8, 9, 10, 12, 13, 16, 17, 18, 21, 23 and 24.

USE EXAMPLE B

Activity in prophylactic treatment of leaves against brown rice-hoppers (*Nilaparvata lugens* Stal)

Rice seedlings (*Oryzae sativa* L.) in the two leaf stage (about 10 per polystyrene pot of size 6.5×6.5 cm) were either untreated or dipped until dripping wet, with an aqueous preparation containing 0.1% of active material. After drying the sprayed leaves, a transparent cylinder was placed over each pot and through an opening, about 30 brown rice-hoppers (*Niliparvata lugens*) in the 4-5 stage, anaesthetised with carbon dioxide, were introduced into each pot. After closing the opening with a fine mesh screen, the pots were kept for 2 days at 28° C. and 16 hours/day of light in the glasshouse, the amount of dead hoppers was determined. The percentage mortality was then estimated and the activity calculated using Abbott's method in comparison with the untreated controls.

The compounds of Example 6 showed an activity of 80% or more.

USE EXAMPLE C

Activity in the prophylactic treatment of feed against the two spotted mite (*Tetranychus urticae* Koch)

From the primary leaf of field beans (*Phaseolus vulgaris nanus Aschers.*) 14 mm diameter discs were cut. Some of these were treated with a 0.1% aqueous preparations of compounds of the invention and these along side untreated discs were placed on filter papers with the underside of the leaves turned upwards. After drying the test pieces, they were each infested with six adult female *Tetranychus urticae* and maintained for 3 days at 25° C. and 16 hours light per day. The experiment was replicated 4 times. Dead and alive adults were then counted and removed. Similarly the number of eggs laid were counted. After a further 7 days, the number of living larvae were counted, the activity calculated using Abbott's method in comparison with the untreated controls.

The compounds of Examples 6 and 18 showed 80-100% total activity against *Tetranychus urticae*.

USE EXAMPLE D

Activity against eggs/larvae of the corn rootworm (*Diabrotica undecimpunctata*)

The compounds of the invention were made up as aqueous emulsions at a concentration of 0.1%. Into the soil in polystyrene petri dishes, containing maize seedlings (1 seedling/dish) and ca. 50 eggs of the corn rootworm (*Diabrotica undecimpunctata*) were pipetted 0.2 ml of these preparations. The closed dishes were left at 25° C. under extended daylight conditions for 7 days. The criterion for judging the activity was the death of eggs or newly hatched larvae at the end of the test.

The compounds of Examples 23, 26, 28 and 29 showed 80-100% activity.

USE EXAMPLE H

Ovicidal activity against eggs of the cotton bollworm (*Heliothis viriscens*)

The compounds of the invention were made up as aqueous preparations at a concentration of 0.1%. One day old eggs that had been laid on filter paper by fertilised female moths were dipped in the preparations until they were completely wet and then placed in closed petri dishes under extended daylight conditions for four days at 25° C. The % inhibition of hatching of the eggs in comparison with untreated eggs indicates the level of activity.

The compound of Examples 6, 26, 28 and 29 showed 80-100% activity.

We claim:

1. 5-Substituted 3-arylisoxazole derivatives of formula I

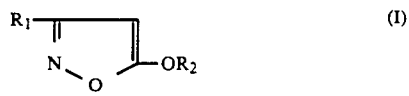

where
$R_1$ is phenyl, biphenyl, naphthyl, furyl, thienyl or pyridyl, each of which is optionally substituted by one or more, of the same or different, halogen, $C_{1-14}$-alkyl, $C_{3-6}$-cycloalkyl, $C_{1-4}$-alkoxy, $C_{1-4}$-alkylthio, di-$C_{1-4}$-alkylamino, $C_{1-6}$-alkoxycarbonyl, halo-$C_{1-4}$-alkyl, halo-$C_{1-4}$-alkoxy, halo-$C_{1-4}$-alkylthio, halo-$C_{1-6}$-alkoxycarbonyl, halo-$C_{3-6}$-cycloalkyl, halo-$C_{3-6}$-cycloalkylmethoxy, halo-$C_{3-6}$-cycloalkylmethylthio, nitro, cyano, amino, phenoxy, halophenoxy, phenylthio or halophenylthio groups, and
$R_2$ is $C_{1-12}$-alkyl, $C_{2-12}$-alkenyl, $C_{2-12}$-alkynyl, $C_{3-6}$-cycloalkyl or $C_{3-6}$-cycloalkylmethyl, each of which is substituted one or more times by the same or different halogen,
wherein each halogen is selected from the group consisting of fluorine, chlorine or bromine.

2. An insecticidal composition which comprises a compound claimed in claim 1, in admixture with an agriculturally acceptable diluent or carrier.

3. A method of combating insects, which comprises applying to the insect or its locus an effective amount of a compound claimed in claim 1.

4. 5-Substituted 3-arylisoxazole derivatives according to claim 1 in which $R_1$ is phenyl optionally monosubstituted by halogen, alkyl or alkoxy and $R_2$ is a fluorine containing alkyl or alkenyl.

5. 5-Substituted 3-arylisoxazole derivatives according to claim 4 in which $R_1$ is phenyl optionally monosubstituted by fluorine, chlorine, methyl or methoxy and $R_2$ is a fluorine containing methyl, ethyl or butenyl group.

6. 5-(3,4,4-Trifluoro-3-butenyl)-3-phenyl isoxazole according to claim 1.

7. An insecticidal composition which comprises a compound claimed in claim 4, in admixture with an agriculturally acceptable diluent or carrier.

8. An insecticidal composition which comprises a compound claimed in claim 5, in admixture with an agriculturally acceptable diluent or carrier.

9. An insecticidal composition which comprises a compound claimed in claim 6, in admixture with an agriculturally acceptable diluent or carrier.

10. A method of combating insects, which comprises applying to the insect or its locus an effective amount of a compound claimed in claim 4.

11. A method of combating insects, which comprises applying to the insect or its locus an effective amount of a compound claimed in claim 5.

12. A method of combating insects, which comprises applying to the insect or its locus an effective amount of a compound claimed in claim 6.

* * * * *